US008322055B1

(12) United States Patent
Saint-Cyr et al.

(10) Patent No.: US 8,322,055 B1

(45) Date of Patent: Dec. 4, 2012

(54) FOOTWEAR WITH INTEGRAL MASSAGER

(76) Inventors: Patrick Saint-Cyr, West Palm Beach, FL (US); Kerry A. Saint-Cyr, West Palm Beach, FL (US)

(*) Notice: Subject to any disclaimer, the term of this patent is extended or adjusted under 35 U.S.C. 154(b) by 607 days.

(21) Appl. No.: 12/380,301

(22) Filed: Feb. 26, 2009

Related U.S. Application Data

(60) Provisional application No. 61/066,989, filed on Feb. 26, 2008.

(51) Int. Cl.
*A61F 5/14* (2006.01)
*A61H 1/00* (2006.01)

(52) U.S. Cl. ........................................... 36/141; 601/46

(58) Field of Classification Search .................... 36/141, 36/132, 137; 601/46, 30, 79
See application file for complete search history.

(56) References Cited

U.S. PATENT DOCUMENTS

| | | | | |
|---|---|---|---|---|
| 4,694,831 | A | 9/1987 | Seltzer | |
| 5,287,638 | A | 2/1994 | Preston | |
| 5,682,690 | A | 11/1997 | Chang | |
| 5,802,743 | A | 9/1998 | Chien | |
| 5,836,899 | A * | 11/1998 | Reilly | 601/46 |
| 5,913,838 | A * | 6/1999 | Reilly | 601/58 |
| 6,234,987 | B1 | 5/2001 | Chen | |
| D474,588 | S | 5/2003 | Dean | |
| 7,013,588 | B2 | 3/2006 | Chang | |
| 7,210,253 | B2 * | 5/2007 | Yu | 36/141 |
| 2005/0126049 | A1 * | 6/2005 | Koenig | 36/141 |
| 2007/0028486 | A1 * | 2/2007 | Montanya et al. | 36/137 |
| 2008/0161734 | A1 * | 7/2008 | Blockton | 601/70 |

* cited by examiner

*Primary Examiner* — Ted Kavanaugh

(74) *Attorney, Agent, or Firm* — Montgomery Patent & Design, LLC; Robert C. Montgomery; Joseph Yakisch

(57) ABSTRACT

An integral massaging means within heel and sole portions within footwear is herein disclosed. The footwear resembles a conventional pair of shoes or sandals with a soft upper area and cushioned soles; however, the sole area is slightly thicker than normal to accommodate a battery pack and a series of vibrating motors across the sole, thereby producing a massaging effect. The duration and intensity of the vibrating motors may be controlled using external control switches and may be activated by pressing an ON/OFF button or by using a remote controller. The massaging apparatus may be activated whether a wearer is sitting down, lying down, or standing upright. User replaceable batteries are provided and accessed through a door located on the bottom of the footwear.

10 Claims, 4 Drawing Sheets

FOOTWEAR WITH INTEGRAL MASSAGER

RELATED APPLICATIONS

The present invention was first described in and claims the benefit of U.S. Provisional Application No. 61/066,989 filed on Feb. 26, 2008, the entire disclosures of which are incorporated herein by reference.

FIELD OF THE INVENTION

The present invention relates generally to footwear and, more particularly, to said footwear comprising an integral, remote-controlled, battery-operated massaging apparatus.

BACKGROUND OF THE INVENTION

Footwear comprises garments worn on the feet for adornment and protection and have been around for thousands of years. In fact the oldest known footwear made of woven sagebrush bark indicates humans have been wearing shoes for ten-thousand (10,000) years. Over the generations footwear has become highly technical and specialized for various activities, including running, hiking, everyday wear, and the like. Boots, sandals, loafers, and slippers made from leather, plastic, rubber, and even wood can be found in shoe stores around the world. Although footwear protects a user's foot and improvements in comfort have increased, regularly wearing shoes can cause feet to become fatigued, uncomfortable, and even damaged over a period of time.

Many people find relaxation and overall comfort from receiving a personal massage. While these massages can be applied virtually anywhere on the human body, one area in particular that is often massaged is the foot. For many people, direct and firm massage to the sole of the foot can reduce muscle aches and pains and even reduce stress and strain. If nothing else, it just feels good. While many people massage their feet immediately after removing their shoes, it is usually only for a limited time and thus the beneficial results are short-lived. While larger automatic massaging devices do exist, most are not specifically designed for the foot and cannot easily be used while at work, while simply waiting for the bus, or while performing any other activity.

Accordingly, there exists a need for a means by which one's feet can protected in a normal manner while always having a means to receive a soothing and relaxing foot massage, still while not encumbering the user from performing other activities. The development of the invention herein described fulfills this need.

Various attempts have been made in the past to overcome these problems and provide for messaging footwear. Among the solutions are several U.S. Pat. No. 4,694,831, issued in the name of Seltzer, describes footwear having an inner sole with an upwardly projecting raised flat foot support and spaced massage bumps which provide a sort of acupressure stimulation to the bottom of a wearer's foot. However, unlike the present apparatus, the Seltzer massage footwear relies heavily on precise location of the acupressure bumps to provide relief and requires the wearer to apply the massaging pressure.

U.S. Pat. No. 5,682,690, issued in the name of Chang, describe footwear having an elongated sole and a plurality of spring-loaded massage rods which provide an opposing pressure point to the bottom of the wearer's foot during walking or other activity. However, unlike the present apparatus, the Chang footwear with adjustable massage units again relies on pressure point locations to provide massaging relief requires the wearer to manually participate in the massage.

U.S. Pat. No. 5,802,743, issued in the name of Chien, describes a massaging slipper having a movable massaging ball mounted to a top surface of the slipper. However, unlike the present apparatus, the Chien structure of massaging slipper does not provide the functionality of everyday footwear.

Other known prior art for footwear with massaging means include U.S. Pat. Nos. 5,287,638 and 6,234,987.

While these devices fulfill their respective, particular objectives and appear to disclose various attempts to provide a means of massaging the foot and providing varying levels of protection; none of the prior art particularly discloses footwear which provide the protection and comfort of everyday shoes and provides for the soothing effects of a foot massage. Accordingly, there exists a need for an apparatus that operates without the disadvantages as described above.

SUMMARY OF THE INVENTION

In view of the foregoing prior art, the inventor recognized a problem and the object of the present apparatus is to solve the aforementioned inherent disadvantages and thus it has been observed that there is need for footwear with integral massager.

To achieve the above objectives, it is an object of the present apparatus to provide footwear having an integral massaging apparatus within a sole portion. The footwear resembles and functions in a substantially similar manner to that of a conventional pair of shoes or sandals comprising a soft upper area and cushioned soles.

A further object of the present apparatus is to provide footwear comprising a sole area which is thicker than conventional shoes in order to accommodate a battery pack and a plurality of vibrating motors dispersed across the sole which provide a soothing massage effect to a bottom portion of a wearer's foot.

Yet still another object of the present apparatus is to provide a plurality of internal vibrating motors which are activated and controlled by a side mounted control switches. The control switches provide a means of turning the massaging effect on and off as well as control the frequency and duration of operation.

Yet still another object of the present apparatus is to provide a time controlling means and an intensity controlling means.

Yet still another object of the present apparatus is to provide an access door which provides the wearer with access to a replaceable power source.

Yet still another object of the present apparatus is to provide a remote control unit which provides a remote means of activating and controlling the massaging effect of the invention via a radio frequency transmitter, receiver and processing unit.

Yet still another object of the present apparatus is provide the wearer with a means of receiving the massaging effect while sitting down, lying down, or standing upright.

Yet still another object of the present apparatus is to provide a method for utilizing footwear with integral massager.

Further objects and advantages of the present apparatus will become apparent from a consideration of the drawings and ensuing description.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

DESCRIPTIVE KEY

Figure 1:
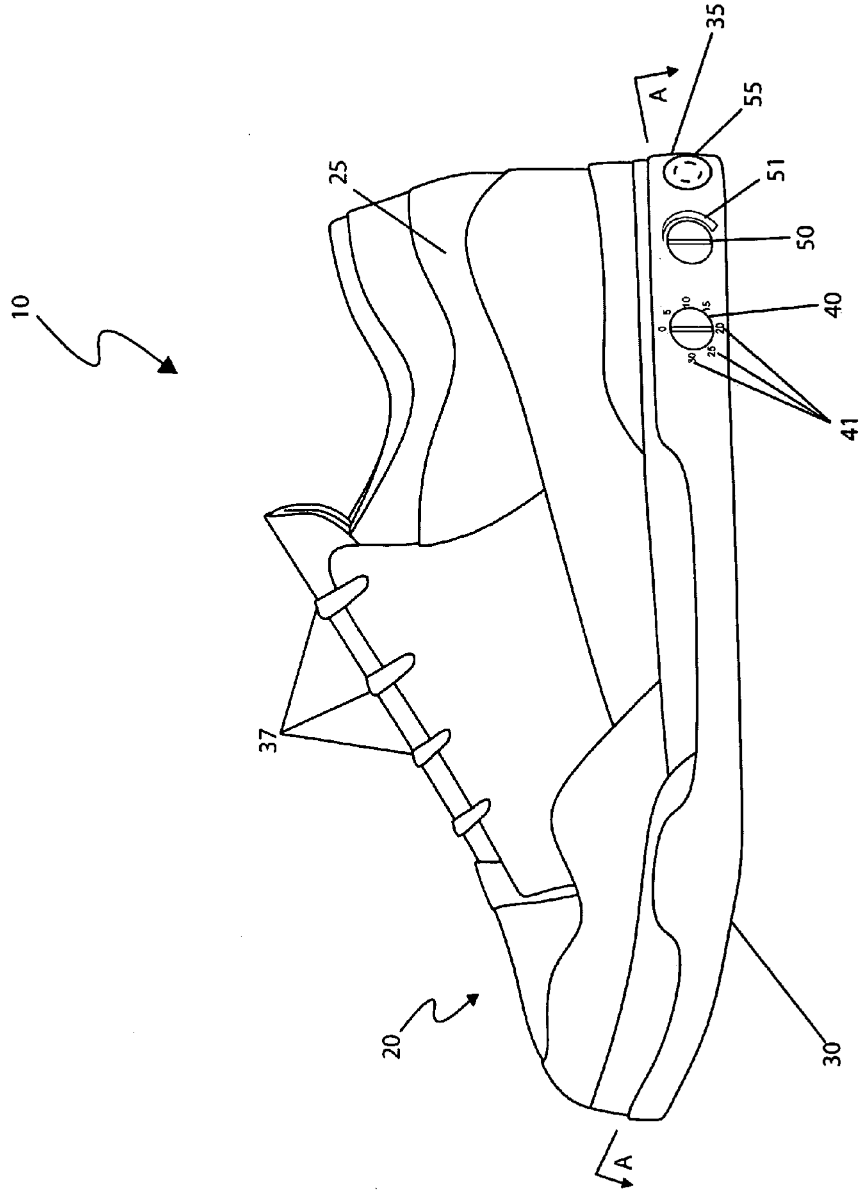
FIG. 1 is a side view of the footwear with integral massager 10, according to a preferred embodiment of the present invention.

10 footwear with integral massager
20 right footwear
22 left footwear
25 footwear upper portion
30 sole portion
35 heel portion
37 lace
40 timer adjustment control
41 timer adjustment indicia
50 intensity adjustment control
51 intensity adjustment indicator
55 ON/OFF switch
60 vibrating motor
62 motor groove
64 wiring
66 radio frequency (RF) receiver/processor unit
70 battery pack compartment
71 battery pack access cover
72 battery pack cover fastener
73 battery pack
75 motor battery
80 remote controller
81 controller case
82 controller battery compartment
83 controller battery compartment cover
84 controller battery
85 controller clip
86 activation button
88 RF transmitter
90 RF signal

DETAILED DESCRIPTION OF THE PREFERRED EMBODIMENT

The best mode for carrying out the invention is presented in terms of its preferred embodiment, herein depicted within FIGS. 1 through 4. However, the invention is not limited to the described embodiment and a person skilled in the art will appreciate that many other embodiments of the invention are possible without deviating from the basic concept of the invention, and that any such work around will also fall under scope of this invention. It is envisioned that other styles and configurations of the present invention can be easily incorporated into the teachings of the present invention, and only one particular configuration shall be shown and described for purposes of clarity and disclosure and not by way of limitation of scope.

The terms "a" and "an" herein do not denote a limitation of quantity, but rather denote the presence of at least one of the referenced items.

The present invention comprises footwear with integral massager (herein described as the "apparatus") 10, which resembles a conventional pair of shoes or sandals comprising a conventional footwear upper portion 25, a cushioned sole portion 30, and a heel portion 35; however, the sole 30 and heel 35 portions are slightly thicker than normal to accommodate an internal massaging vibration means comprising a battery 73, a plurality of vibrating motors 60, and an RF receiver/processor unit 66. Said massaging vibration means is activated by a side-mounted ON/OFF switch 55 or a handheld remote controller 80. The vibrating function of the apparatus 10 may be utilized whether a wearer is sitting down, lying down, or even standing up. The wearer is able to select a timed duration and intensity of a vibrating cycle via a timer adjustment control 40 and an intensity adjustment control 50 also located along a side surface of the heel portion 35. A user replaceable battery pack 73 is provided through a battery pack access cover 71 on the bottom of the heel portion 35.

Referring now to FIG. 1, a side view of the apparatus 10, according to a preferred embodiment of the present invention, is disclosed. A right footwear portion 20 of the apparatus 10 is depicted here; however, it is understood that the apparatus 10 is to be sold and provided as a pair of matching footwear in a normal manner including a left footwear portion 22. Said footwear portions 20, 22 of the apparatus 10 are envisioned to be made of conventional natural and synthetic materials such as, but not limited to: leather, vinyl, cotton, rubber, or the like. These materials are all readily available and well known to manufacturers of goods of this type. The footwear upper portion 25 of the apparatus 10 comprises an assembly of cut shapes corresponding thereto various sizes and styles of footwear according to a pattern, and sewn together using commercial heavy-duty sewing machines. The sole portion 30 would be made of materials such as, but not limited to: various rubber compositions, various synthetic materials, or a combination of materials including leather. The sole portion 30 would be made in an injection molding process or in a combination of injection molding and sewing processes. This fabrication process would require the design and use of custom injection molds and possibly heavy-duty sewing machines.

Figure 2:
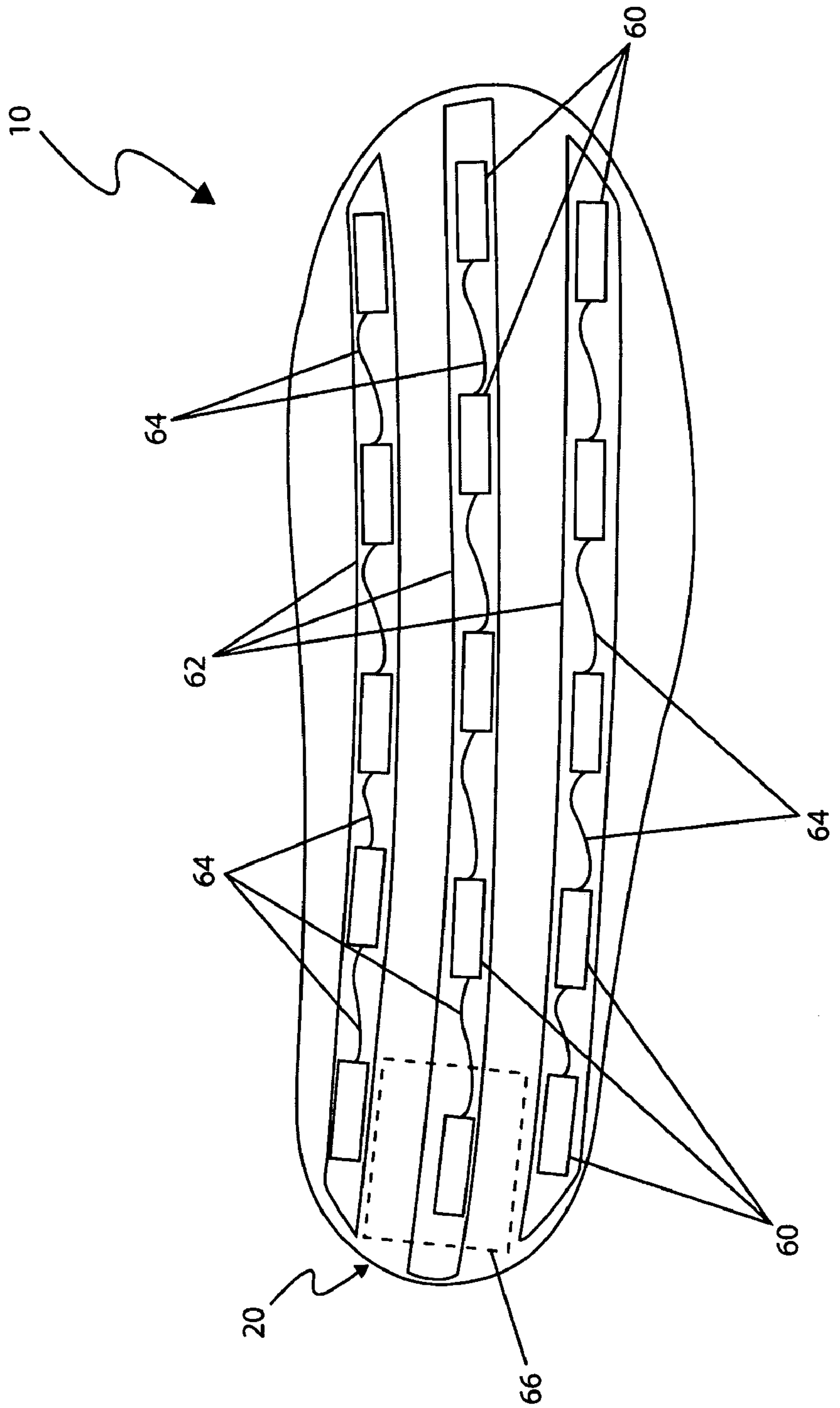
FIG. 2 is a sectional view as taken along section A-A (see FIG. 1) of the footwear with integral massager 10, according to a preferred embodiment of the present invention.

The right 20 and left 22 footwear portions both provide a foot massaging means via an internal vibrating mechanism comprising a plurality of battery-powered vibrating motors 60 spread across an inner top surface of the sole portion 30 (see FIG. 2). A plurality of user accessible vibration controls are also provided and arranged in a mirror-image manner along each inwardly-facing heel portion 35 of said footwear 20, 22. Said vibration control components comprise a timer adjustment control 40, a plurality of timer adjustment indicia 41, an intensity adjustment control 50, an intensity adjustment indicator 51, and an ON/OFF switch 55. The timer adjustment control 40 provides a means to manually select a duration of time as indicated by the timer adjustment indicia 41, thereby energizing the vibrating motors 60 for a set period of time following receipt of an activation signal either from the ON/OFF switch 55 or the remote controller 80 (see FIG. 4). The intensity adjustment control 50 provides a manual means to increase or decrease a voltage thereto the vibrating motors 60, subsequently increasing or decreasing a respective revolution per minute (RPM) speed of said vibrating motors 60. The timer adjustment control 40 and the intensity adjustment control 50 comprise common finger operated miniature rotary rheostatic-type electrical components designed to deliver a user selected variable voltage signal thereto an RF receiver/processor unit 66 located therein the heel portion 35. The ON/OFF switch 55 comprises a push-on/push-off contact closure component having a protective external rubber diaphragm-type cover to seal out harmful elements. Said controls 40, 50, 55 and their associated electrical equipment would be integrally molded thereinto the heel portions 35 of the apparatus 10. The timer adjustment indicia 41 and intensity adjustment indicator 51 comprise raised molded communicating features marked with a colored ink (see FIGS. 2 and 3).

Referring now to FIG. 2, a sectional view as taken along section A-A (see FIG. 1) of the apparatus 10, according to the preferred embodiment of the present invention, is disclosed. This sectional view of the sole portion 30 shows one possible arrangement of the vibrating motors 60 and their associated electrical wiring 64 mounted therewithin a plurality of parallel motor grooves 62 extending in a linear fashion in a front to rear direction. Said motor grooves 62 comprise linear molded-in recessed areas comprising a width and depth being suitable to contain a plurality of vibrating motors 60. The vibrating motors 60 comprise miniature cylindrical-bodied units similar to those used to generate vibration in common cellular telephones. The vibrating motors 60 are affixed therewithin said grooves 62 preferably using adhesives or may be incorporated therein the aforementioned molding process of the sole 30 and heel 35 portions. It is understood that an actual number of vibrating motors 60 and corresponding groove portions 62 may be provided to result in a desired massaging affect thereto a wearer's feet and as such should not be interpreted as a limiting factor of the apparatus 10.

Figure 3:
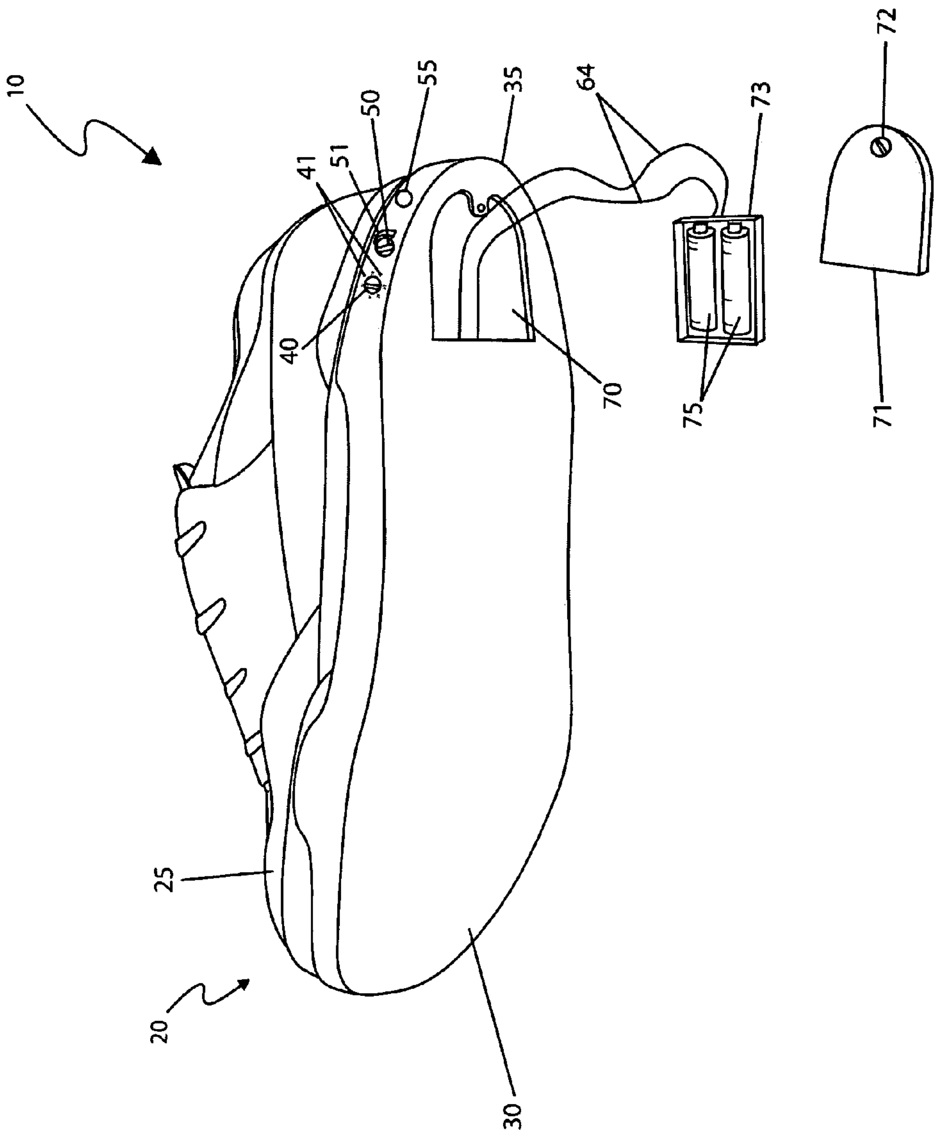
FIG. 3 is a bottom perspective view of the footwear with integral massager 10, according to a preferred embodiment of the present invention; and, FIG. 4 is an electrical block diagram of the footwear with integral massager 10, according to a preferred embodiment of the present invention.

Referring now to FIG. 3 a bottom perspective view of the apparatus 10, according to the preferred embodiment of the present invention, is disclosed. The apparatus 10 comprises a battery pack compartment 70, a battery pack access cover 71, a battery pack cover fastener 72, a battery pack 73, and one (1) or more motor batteries 75, each of which is discreetly enclosed therewithin the heel portion 35 when fully assembled. The battery pack 73 comprises a conventional battery holder device capable of retaining and electrically connecting one (1) or more standard disposable or rechargeable motor batteries 75 therewithin. The battery pack access cover 71 is retained therein a closed state via a battery pack cover fastener 72 providing a common half-turn release function using a coin or small tool.

The battery pack compartment 70 and the battery pack access cover 71 are made using similar materials as the heel portion 35 and manufactured in an injection-molding process. The vibrating motors 60, wiring 64, the RF receiver/processor unit 66, the timer adjustment control 40, the intensity adjustment control 50, and the battery pack compartment 70, would be molded thereinto the sole 30 and heel 35 portions.

Figure 4:
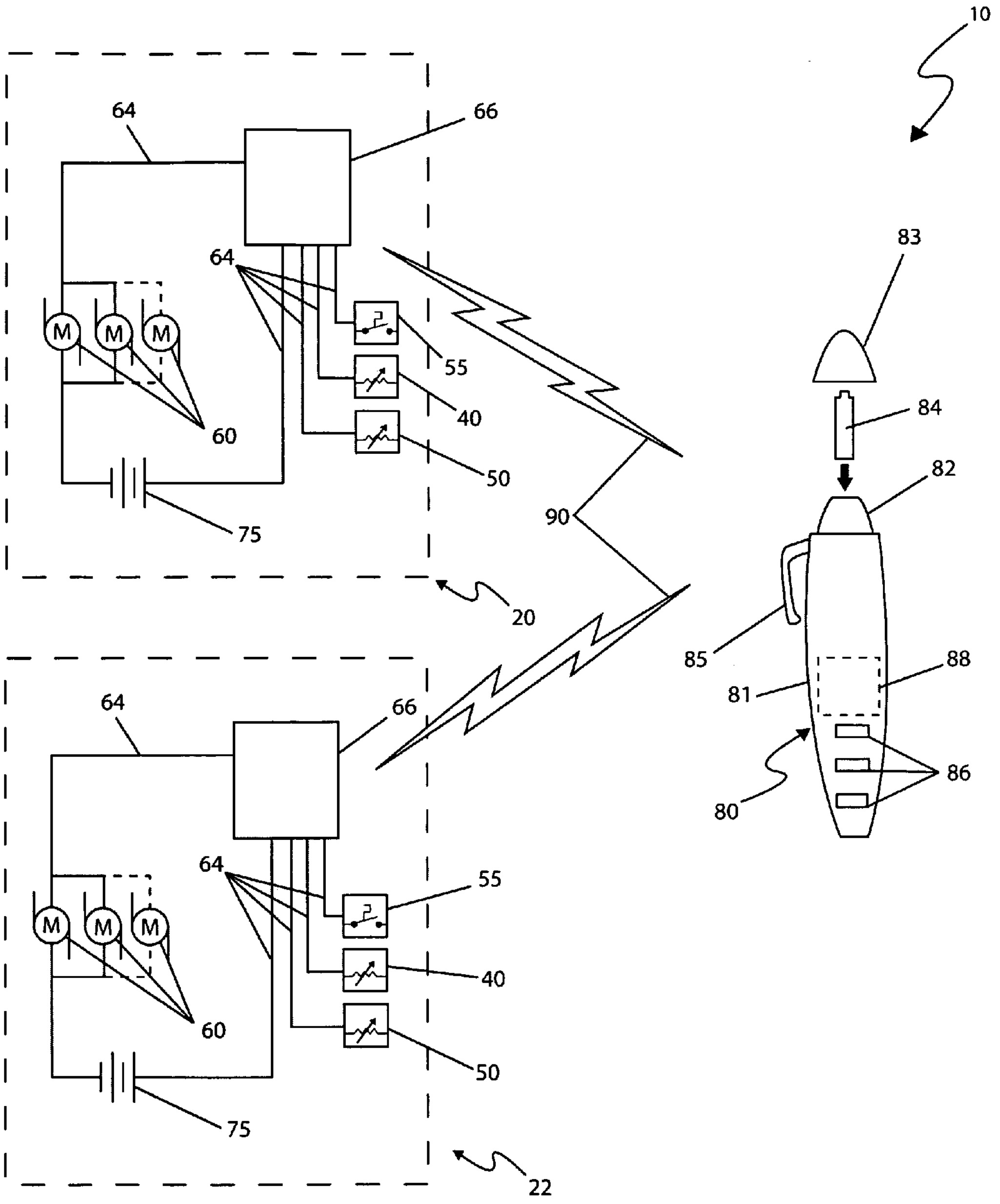

Referring now to FIG. 4 an electrical block diagram of the apparatus 10, according to the preferred embodiment of the present invention, is disclosed. The block diagram shows how the previously described motor batteries 75, timer adjustment control 40, intensity adjustment control 50, ON/OFF switch 55, and vibrating motors 60, are interconnected via common insulated wiring 64 therewith a microprocessor-based RF receiver/processor unit 66. The RF receiver/processor unit 66 comprises a common rectangular plastic enclosure thereto internal electrical and electronic components such as, but not limited to: one (1) or more microprocessors, a printed circuit board, relays, and various components, being necessary to operate the vibrating function of the apparatus 10. The number of motors 60 may vary based on a desired vibrating affect and/or a size of the footwear 20, 22.

The remote controller 80 is comprised of a controller case 81, a controller battery compartment 82, a controller battery compartment cover 83, a controller battery 84, a controller clip 85, three (3) controller buttons 86, and an RF transmitter 88. The remote controller 80 is envisioned to be powered by a disposable or rechargeable battery 84 and comprises a controller case 81 having an external linear shape similar to that of a writing pen. The controller case 81 is to be sized such that it may be affixed thereto a chest pocket via a controller clip 85 or be conveniently stored therewithin a purse. The controller battery compartment cover 83 comprises a dome-shaped snap-on cap to enclose a cylindrical-shaped controller battery compartment 82 located therewithin the controller case 81. The controller battery compartment cover 83 also provides an electrical connection means thereto the controller battery 84 in an expected manner. The controller buttons 86 provide selective activation of an internal transmitter 88 which in-turn transmits an RF signal 90 having a correspondingly configured frequency so as to preferably activate the right footwear 20 and the left footwear 22 separately, or both footwear 20, 22 simultaneously; however, any number of controller buttons 86 may be provided enabling additional functionality such as remote timer and intensity adjustment, selecting various vibration patterns, or the like, and as such should not be interpreted as a limiting factor of the apparatus 10.

The electrical components of the apparatus 10 including the battery pack compartment 70, the vibrating motors 60, the timer 40 and intensity 50 adjustment controls, the RF receiver/processor unit 66, the interconnecting wiring 64, and the remote controller 80, would best be obtained from wholesalers and manufactures that deal in goods of that nature, and assembled at a final location.

The preferred embodiment of the present invention can be utilized by the common user in a simple and effortless manner with little or no training. After initial purchase or acquisition of the apparatus 10, the user simply needs to wear the footwear 20, 22 as any normal pair of shoes or sandals. The apparatus 10 could then be worn for normal daily use just as any other shoe, or if the user wants a soothing foot massage, the ON/OFF switch 55 or remote controller 80 may be utilized to activate the vibrating motors 60 of the apparatus 10, and adjusted for a desired cycle duration and vibration intensity.

The method of utilizing the apparatus 10 may be achieved by the following steps: installing one (1) or more fresh motor batteries 75 therein the heel portion 35 of each of the footwear 20, 22 using the battery pack access cover 71 and the battery pack cover fastener 72; installing a fresh controller battery 84 therewithin the remote controller 80 using the controller battery compartment cover 83; putting both footwear portions 20, 22 of the apparatus 10 upon a wearer's feet as they would any normal pair of shoes or sandals; wearing said footwear 20, 22 to walk or stand in a normal manner until desiring a foot massage; rotating each of the two (2) timer adjustment controls 40 with a finger or thumb to set the length of time a massaging vibration will last once activated; rotating each of the two (2) intensity adjustment controls 50 with a finger or thumb to adjust the intensity of the massage based upon a user's preference; pressing the ON/OFF switch 55 thereupon one (1) or both footwear portions 20, 22 to activate the vibrating motors 60; or alternately activating said motors 60 using the remote controller 80 in like manner using the activation buttons 86; massaging one (1) or both feet in a soothing and relaxing manner while sitting, laying down, or standing, thereby allowing the user to perform other activities.

The battery pack 73 may comprise either a disposable type or a rechargeable type motor battery 75. After significant use of the massage function of the apparatus 10, said motor batteries 75 will need to be replaced or recharged. In the case of a disposable battery 75, replacement may be accomplished by performing the following steps: loosening the battery pack cover fastener 72; removing the battery pack compartment cover 71; removing the battery pack 73 from the battery pack compartment 70; removing the motor batteries 75 therefrom the battery pack 73; installing fresh motor batteries 75 thereinto the battery pack 73; installing the battery pack 73 thereinto the battery pack compartment 70; placing the battery pack compartment cover 71 back onto the heel portion 35; rotating the battery pack cover fastener 72 using a coin or small tool. In the case of a rechargeable motor battery 75, the process would be the same except that once the motor battery 75 is removed, it would need to be charged using a suitable commercially available charging device and then placed back into the battery pack compartment 70 in a similar manner as the previously described disposable battery 75.

The foregoing descriptions of specific embodiments of the present invention have been presented for purposes of illustration and description. They are not intended to be exhaustive or to limit the invention and method of use to the precise forms disclosed. Obviously many modifications and variations are possible in light of the above teaching. The embodiment was chosen and described in order to best explain the principles of the invention and its practical application, and to thereby enable others skilled in the art to best utilize the invention and various embodiments with various modifications as are suited to the particular use contemplated. It is understood that various omissions or substitutions of equivalents are contemplated as circumstance may suggest or render expedient, but is intended to cover the application or implementation without departing from the spirit or scope of the claims of the present invention.

What is claimed is:

1. A combined footwear and massaging apparatus for providing therapeutic relief, said combined footwear and massaging apparatus comprising:
- a footwear adapted to be positioned on a user foot, said footwear having a sole formed therein and spaced above a bottom most surface of said footwear; and,
- a massaging apparatus integrally formed with said footwear, said massaging apparatus comprising:
  - a plurality of grooves spaced along said sole of said footwear;
  - a plurality of vibrating transducers each affixed within one of said plurality of grooves;
  - a timer adjustment control electrically coupled to said plurality of vibrating transducers;
  - an intensity adjustment control electrically coupled to said plurality of vibrating transducers;
  - a battery compartment formed in said sole of said footwear, accessible from said bottom most surface; and,
  - a power source removably housed within said battery compartment and being electrically coupled to said plurality of vibrating transducers as well as said timer adjustment control and said intensity adjustment control respectively;
- wherein an intensity level of said plurality of vibrating transducers is selectively adjustable by a user; and,
- wherein said plurality of vibrating transducers are automatically toggled to an off mode after a predetermined time period has lapsed.

2. The combined footwear and massaging apparatus of claim 1, wherein said massaging apparatus further comprises:
- a receiver electrically coupled to said timer and intensity adjustment controls respectively; and,
- a remote control in wireless communication with said receiver for controlling a frequency and intensity of said plurality of vibrating transducers respectively, said remote control further comprising:
  - a remote control case suitably sized and shaped for being carried by the user; and,
  - a remote control clip attached to said remote control case.

3. The combined footwear and massaging apparatus of claim 2, wherein said plurality of grooves are molded into said sole of said footwear, said plurality of grooves being oriented into a plurality of parallel columns spanning along a major longitudinal length of said sole.

4. The combined footwear and massaging apparatus of claim 3, wherein said timer and intensity adjustment controls are positioned along an outer edge of said footwear for allowing a user to manually adjust a duration and frequency of said plurality of vibrating transducers.

5. The combined footwear and massaging apparatus of claim 4, wherein said battery compartment is positioned at a heel portion of said sole.

6. A combined footwear and massaging apparatus for providing therapeutic relief, said combined footwear and massaging apparatus comprising:
- a footwear adapted to be positioned on a user foot, said footwear having a sole formed therein and spaced above a bottom most surface of said footwear; and,
- a massaging apparatus integrally formed with said footwear, said massaging apparatus comprising:
  - a plurality of grooves spaced along said sole of said footwear
  - a plurality of vibrating transducers each affixed within one of said plurality of grooves;
  - a timer adjustment control electrically coupled to said plurality of vibrating transducers;
  - an intensity adjustment control electrically coupled to said plurality of vibrating transducers;
  - a battery compartment formed in said sole of said footwear; and,
  - a power source removably housed within said battery compartment and being electrically coupled to said plurality of vibrating transducers as well as said timer adjustment control and said intensity adjustment control respectively;
- wherein an intensity level of said plurality of vibrating transducers is selectively adjustable by a user;
- wherein said plurality of vibrating transducers are automatically toggled to an off mode after a predetermined time period has lapsed; and,
- wherein said plurality of vibrating transducers include vibrating motors connected in series to said power source.

7. The combined footwear and massaging apparatus of claim 6, wherein said massaging apparatus further comprises:
- a receiver electrically coupled to said timer and intensity adjustment controls respectively; and,
- a remote control in wireless communication with said receiver for controlling a frequency and intensity of said plurality of vibrating transducers respectively, said remote control further comprising:
  - a remote control case suitably sized and shaped for being carried by the user; and,
  - a remote control clip attached to said remote control case.

8. The combined footwear and massaging apparatus of claim 7, wherein said plurality of grooves are molded into said sole of said footwear, said plurality of grooves being oriented into a plurality of parallel columns spanning along a major longitudinal length of said sole.

9. The combined footwear and massaging apparatus of claim 8, wherein said timer and intensity adjustment controls are positioned along an outer edge of said footwear for allowing a user to manually adjust a duration and frequency of said plurality of vibrating transducers.

10. The combined footwear and massaging apparatus of claim 9, wherein said battery compartment is positioned at a heel portion of said sole.

* * * * *